United States Patent [19]

Fry et al.

[11] Patent Number: 4,539,640

[45] Date of Patent: Sep. 3, 1985

[54] RECONSTRUCTION SYSTEM AND METHODS FOR IMPEDANCE IMAGING

[75] Inventors: Bradley Fry; Alvin Wexler, both of Winnipeg, Canada

[73] Assignee: Tasc Ltd., Winnipeg, Canada

[21] Appl. No.: 407,275

[22] Filed: Aug. 10, 1982

[30] Foreign Application Priority Data

Jan. 12, 1982 [CA] Canada .................................. 393977

[51] Int. Cl.$^3$ ............................................. G06F 15/42
[52] U.S. Cl. ..................................... 364/414; 128/734
[58] Field of Search ................ 364/414; 128/734, 644, 128/639

[56] References Cited

U.S. PATENT DOCUMENTS

| | | | |
|---|---|---|---|
| 3,294,084 | 12/1966 | Schuler et al. | 128/2.06 |
| 3,320,418 | 5/1967 | Steel | 250/71.5 |
| 3,452,743 | 7/1969 | Rieke | 128/2.1 |
| 3,608,543 | 9/1971 | Longini et al. | 128/2.1 R |
| 3,695,252 | 10/1972 | Gordon | 128/2 V |
| 3,717,141 | 2/1973 | Krohn et al. | 128/644 |
| 3,750,649 | 8/1973 | Severinghaus | 128/2.1 Z |
| 3,787,827 | 1/1974 | Stout | 340/174.1 P |
| 3,835,840 | 9/1974 | Mount | 128/2.05 V |
| 3,847,466 | 11/1974 | Forse | 350/7 |
| 3,874,368 | 4/1975 | Asrican | 128/2.1 Z |
| 3,908,128 | 9/1975 | Richey | 250/366 |
| 3,970,852 | 7/1976 | Richey et al. | 350/363 S |
| 3,971,366 | 7/1976 | Motoyama | 128/639 |
| 3,980,073 | 9/1976 | Shaw, IV | 128/2 H |
| 3,996,924 | 12/1976 | Wheeler | 128/2.05 V |
| 4,066,900 | 1/1978 | Le May | 250/360 |
| 4,066,902 | 1/1978 | Le May | 250/363 |
| 4,066,903 | 1/1978 | Le May | 250/363 S |
| 4,066,906 | 1/1978 | Hounsfield et al. | 250/445 T |
| 4,070,581 | 1/1978 | Gibbons et al. | 250/445 T |
| 4,071,760 | 1/1978 | Le May | 250/363 S |
| 4,071,771 | 1/1978 | Covic et al. | 250/505 |
| 4,072,875 | 2/1978 | Webley | 313/60 |
| 4,074,564 | 2/1978 | Anderson | 73/596 |
| 4,075,700 | 2/1978 | Blay | 364/515 |
| 4,076,985 | 2/1978 | Le May | 250/445 T |
| 4,081,681 | 3/1978 | Froggatt | 250/360 |
| 4,084,093 | 4/1978 | Marsh et al. | 250/360 |
| 4,084,094 | 4/1978 | Froggatt | 250/445 T |
| 4,088,887 | 5/1978 | Le May | 250/366 |

(List continued on next page.)

OTHER PUBLICATIONS

*An Impedance Camera for Spatially Specific Measurement of Thorax*, Henderson et al., IEEE BME-25, 5/78.
*Imaging of Electrical Conductivity: CT Technique,* LeRoy Price, SPIE, vol. 206, 1979.
*Computerized Brain Impedograph,* Leon Adam, 7ITJ, Life Sci., 1977, vol. 7.
*Electrical Impedance Brain Scanner,* Benabid et al., 717, Life Sci., 1978, vol. 8.
*Algebrai Reconstruction of Spatial Distributions,* Greenleaf et al., NBS Pub. 453, 1975.
"A Limitation in Systems for Imaging Electrical Conductivity Distributions", Bates et al., IEEE Trans. on Biomedical Engineering (vol. BME-27, No. 7, Jul. 1980, pp. 418–420).

*Primary Examiner*—Jerry Smith
*Assistant Examiner*—Louis Woo
*Attorney, Agent, or Firm*—Spencer & Frank

[57] ABSTRACT

A method and apparatus for imaging the interior of a structure, such as a mineral or human body, having regions therein which differentially affect particular characteristics of electrical signals transmitted through the body. The method involves injecting a plurality of electrical signals into the body, measuring at least one characteristic of each such signal at a plurality of locations, comparing the measured characteristic with the corresponding characteristic measured at at least one reference point of the structure and generating comparison signals, iteratively reconstructing the impedance spatial relationships between the regions within the structure by utilizing the comparison signals, and providing an image of the interior of the structure from the reconstruction of such impedance spatial relationships.

18 Claims, 5 Drawing Figures

U.S. PATENT DOCUMENTS

| | | | |
|---|---|---|---|
| 4,091,285 | 5/1978 | Logan et al. | 250/360 |
| 4,091,286 | 5/1978 | Logan et al. | 250/360 |
| 4,091,287 | 5/1978 | Hounsfield | 250/362 |
| 4,091,289 | 5/1978 | Le May | 250/445 T |
| 4,096,390 | 6/1978 | Hounsfield | 250/445 T |
| 4,097,744 | 6/1978 | Le May | 250/366 |
| 4,097,746 | 6/1978 | Ingham et al. | 250/444 |
| 4,101,768 | 7/1978 | Lill | 250/360 |
| 4,101,773 | 7/1978 | Le May et al. | 250/401 |
| 4,103,169 | 7/1978 | Hounsfield | 250/445 T |
| 4,115,691 | 9/1978 | Oldendorf | 250/312 |
| 4,115,695 | 9/1978 | Kelman | 250/445 T |
| 4,115,696 | 9/1978 | Truscott | 250/445 T |
| 4,115,697 | 9/1978 | Hounsfield et al. | 250/445 T |
| 4,115,698 | 9/1978 | Hounsfield | 250/445 T |
| 4,117,366 | 9/1978 | Davis | 313/95 |
| 4,263,920 | 4/1981 | Tasto et al. | 128/734 |
| 4,300,574 | 11/1981 | Briggs | 128/734 |

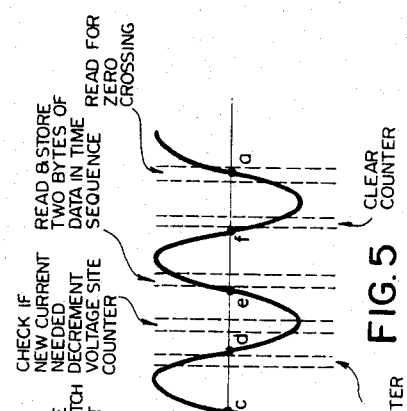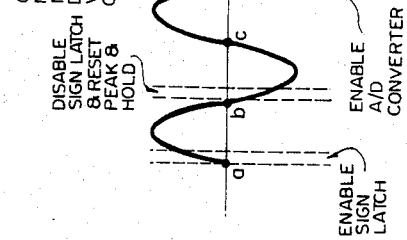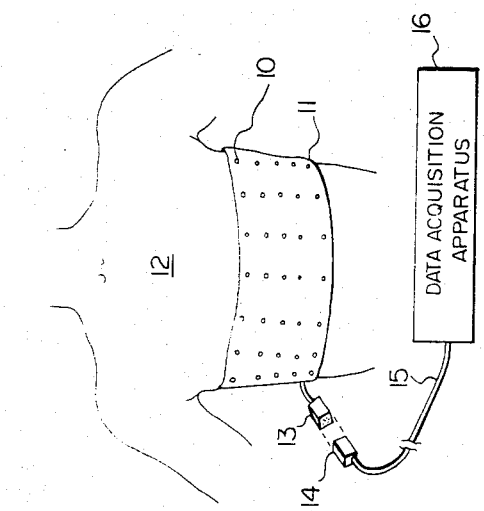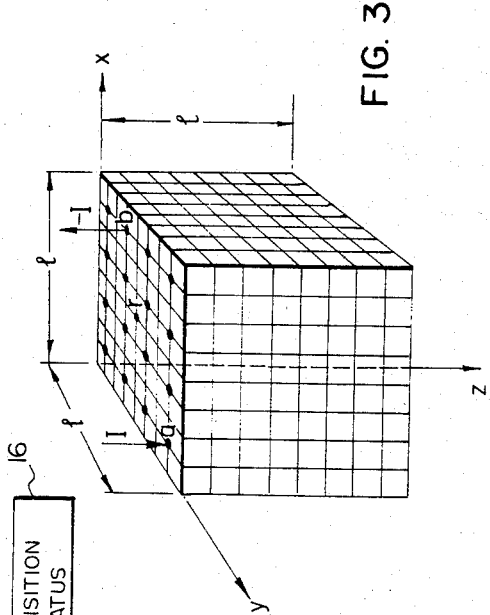

RECONSTRUCTION SYSTEM AND METHODS FOR IMPEDANCE IMAGING

BACKGROUND OF THE INVENTION

The present invention relates to an electrical method of imaging sub-surface structures within a body having differing electrical impedances, by measurement of surface or internal potentials caused by impressed currents applied externally or internally to the body. The term "impedance" is to be understood in the generic sense, relating to the ratio from time to time of voltage to current during transient signal responses (e.g. pulses) as well as during steady-state signal responses.

Electrical impedance methods have been used in geological and mineral prospecting applications. For a summary of typical methods used in these applications, reference may be made to the textbook *Applied Geophysics* by Telford, Geldart, Sheriff and Keys, published by Cambridge University Press (1976). At page 632 of this text, it is pointed out that all resistivity (or, more generally, "impedance") methods employ an artificial source of current which is introduced into the ground through point electrodes or long line contacts. The procedure then is to measure potentials at other electrodes in the vicinity of the current flow. In most cases, the current is also noted; it is then possible to determine an effective or apparent resistivity of the subsurface. The authors further stated:

"In this regard the resistivity technique is superior, theoretically at least, to all the other electrical methods, since quantitative results are obtained by using a controlled source of specific dimensions. Practically—as in the other geophysical methods—the maximum potentialities of resistivity are not usually realized. The chief drawback is its large sensitivity to minor variations in conductivity near the surface; in electronic parlance the noise level is high. An analogous situation would exist in magnetics if one were to employ a magnetometer with sensitivity in the milligamma range. This limitation, added to the practical difficulty involved in dragging several electrodes and long wires over rough wooded terrain, has made the electromagnetic method more popular than resistivity in mineral exploration. Nor is resistivity particularly suitable for oil prospecting."

Thus, while the theoretical possibilities and advantages of resistivity techniques are recognized by Telford et al, the practical shortcomings of typical embodiments of such techniques are stated to be sufficiently serious that electromagnetic methods are more popular—at least in mineral exploration—and of course, they also state that "resistivity" is not particularly suitable for oil prospecting.

Electrical impedance methods have also been used in the medical field to measure certain overall cardiac parameters, intrathoracic fluid volumes, etc. Examples of such methods are disclosed in U.S. Pat. Nos. 3,750,649 (Severinghaus) issued Aug. 7, 1973; 3,294,084 (Schuler et al) issued Dec. 27, 1966; 3,452,743 (Rieke) issued July 1, 1969; 3,608,543 (Longini et al) issued Sept. 28, 1971; 3,835,840 (Mount) issued Sept. 17, 1974; 3,874,368 (Asrican) issued Apr. 1, 1975; 3,996,924 (Wheeler) issued Dec. 14, 1976; and 3,980,073 (Shaw) issued Sept. 14, 1976. However, none of the foregoing references deal with imaging of internal organs but merely with measurement of overall cardiac parameters.

Recently, computer processing of X-ray absorption data has been used to produce images of internal organs. One of the most active companies in the use of computerized axial tomography has been E.M.I. Ltd., which is the assignee of numerous patents in this field, including U.S. Pat. Nos. 3,847,466 issued Dec. 12, 1974; 4,066,900, 4,066,902, 4,066,903 and 4,066,906 issued Jan. 3, 1978; 4,070,581 issued Jan. 24, 1978; 4,071,760 issued Jan. 31, 1978; 4,072,875 issued Feb. 7, 1978; 4,075,700 issued Feb. 21, 1978; 4,076,985 issued Feb. 28, 1978; 4,081,681 issued Mar. 28, 1978; 4,084,093 and 4,084,094 issued Apr. 11, 1978; 4,088,887 issued May 9, 1978; 4,091,285; 4,091,286; 4,091,287 and 4,091,289 issued May 23, 1978; 4,096,390 issued June 20, 1978; 4,097,744 and 4,097,746 issued June 27, 1978; 4,101,768 and 4,101,773 issued July 18, 1978; 4,103,169 issued July 25, 1978; 4,115,691; 4,115,697 and 4,115,698 issued Sept. 19, 1978; and 4,117,366 issued Sept. 26, 1978. Another company active in radiation scanning techniques is Ohio Nuclear, Inc., the assignee of various patents in the field, including U.S. Pat. Nos. 3,320,418 isssued May 16, 1967; 3,695,252 issued Oct. 3, 1972; 3,787,827 issued Jan. 22, 1974; 3,908,128 issued Sept. 23, 1975; 3,970,852 issued July 20, 1976; and 4,071,771 issued Jan. 31, 1978. General Electric Company has patents in the field of computerized tomography scanning including U.S. Pat. Nos. 4,115,695 and 4,115,696 issued Sept. 19, 1978. As may be observed from consideration of the foregoing patents, computerized radiation tomography is complex and expensive. The mechanics of the various techniques and equipment employed are large, costly and comparatively slow and they cannot be used to follow dynamic activity of organs. Perhaps most importantly, radiation techniques are hazardous—especially for their long-term effects.

An imaging and reconstruction technique which has been of some interest recently involves the use of ultrasonics. U.S. Pat. No. 4,074,564 of Varian Associates, Inc., issued Feb. 21, 1978, teaches that short bursts of ultrasonic energy may be directed through a three-dimensional specimen to determine the spatial distribution of those structures within the specimen capable of affecting the waveform of the energy. Transducers are placed in spaced positions about the periphery of the specimen to measure the affected parameters (such as attenuation and delay time) of the energy as a result of passing through the specimen along paths between the spaced transducers. The output signals containing this transit time and energy absorption information may be retained in a data storage device. Through conventional programming techniques, a computer processes the data and calculates a velocity or absorption profile for each path. The profiles are collectively used to reconstruct two-dimensional or three-dimensional images of the specimen. Analog reconstruction methods are also used. However effective ultrasonic imaging and reconstruction techniques may be, it is suspected that they suffer from the same general drawback as X-ray or radiation scanning techniques,—i.e. they are hazardous to health. Indeed, it is widely thought that ultrasonic energy absorbed by a living body can cause genetic damage. Also, ultrasonic imaging presents only a restricted field of view.

Unlike X-rays or ultrasonic energy, low-magnitude electric currents are not known to have adverse effects upon animals or humans. For this reason, electrical impedance measurement techniques have been of interest in the medical field, but have been insufficiently researched to be useful in the reconstruction and imaging of internal organs. Henderson, Webster and Swanson in "A Thoracic Electrical Impedance Camera" (29th ACEMB Digest, P. 332) showed that the lung fields can be mapped in spite of their simplified assumption that currents flow in beam-like fashion through the thorax. However, their approach can only produce a surface map influenced by the lung and lung-water distribution. Such results may permit interpretation of physiological phenomena but cannot directly produce tomographic images.

Using the electrical approach it has been proposed by workers in the field to obtain tomographic images, but such workers have invariably been deterred by the fact that the electrical currents injected into the body being imaged do not travel in straight lines but rather spread out and take many different paths. Since this has been perceived as a problem, it has been attempted to utilize "guard electrodes" which surround the primary electrodes and which prevent or at least restrict the spreading out of the current flowing between the primary electrodes—see, for example, the aforesaid U.S. Pat. Nos. 3,750,649; 3,452,743 and 3,608,543. However, the guard ring approach cannot be totally effective to constrain the currents to straight-line flow.

In electrical imaging methods that assume beam-like or straight-line current flow, voltages must be measured at or very near to active electrodes through which current is impressed upon the body. In doing this, there is an implicit and incorrect parallel drawn with X-ray tomography. The assumption that the currents travel as beams—whether straight or curved—does not correspond with actuality and results in consequent errors due to improper modelling of flow path, shape, width and length, that would obscure detail in fine structures—see R. H. T. Bates et al, "A Limitation on Systems for Imaging Electrical Conductivity Distributions"—I.E.E.E. Transactions on Biomedical Engineering, Vol. BME-27, No. 7, July, 1980—pp. 418–420. Moreover, the necessity for measurement of a voltage at an active current electrode causes the inclusion of the effect of contact resistance to degrade measurements that must be accurate in order to produce fine detail. The measurement of voltages very near to an active electrode, because of the steep voltage gradient in the vicinity of the electrode, would also result in significant inaccuracy.

SUMMARY OF THE INVENTION

Thus, an object of the present invention is to provide a method of electrical imaging of a subsurface structure, which method is neither degraded by the erroneous assumption that the current flow within the structure follows beam-like paths nor constrained by attempting to confine the current flow to such paths by use of guard rings or the like. Indeed, it is an advantage of the invention that useful rather than confusing information is derived from the spreading of the current paths throughout the structure.

The electrical imaging technique of this invention recognizes, for example, that various organs of the body have differing resistivities, and that resistivity varies inhomogenously even within a given organ—for example, the resistivity of human blood is roughly 100–130 ohm-cm; that of skeletal muscle varies over the range of 100–700 ohm-cm; fat ranges over 1000–5000 ohm-cm; and bone is 2000–16000 ohm-cm. However, in the present invention, the exact values of conductivity need not be known in advance—it is only required that resistivity differences be significant. It may also be noted that whereas a vein or artery can be viewed almost as a current-carrying wire, a blood clot is akin to an insulator. This fact enables the method to be used in the location of blood clots. Tumors also have resistivity patterns differing from the surrounding tissue and the method therefore permits their identification in a primary fashion rather than through secondary effects as is often the case with X-ray measurements.

Thus, according to the invention, there is provided a method and apparatus for reconstructing an internal image of a structure having regions which differentially affect particular characteristics of electrical signals passed therethrough. A plurality of electrical signals are injected into the structure in time sequence or as multiplex signals through input sites located either upon the surface of the structure or internally thereof, causing current flow along a plurality of paths through each region which terminate in output sites located upon or within the structure. At least one characteristic of each signal—such as amplitude, phase or waveform—is measured at a plurality of locations which are preferably remote from the input and output sites. (By "remote" is meant sufficiently removed from the current input and output sites that the steep voltage gradients, which inevitably exist in the immediate vicinity of such sites, do not affect the measurements). The measured characteristic or characteristics is or are compared with the corresponding characteristic or characteristics of the signal measured at one or more reference points upon or within the structure and the comparison signals obtained are utilized to mathematically reconstruct the spatial relationships between the regions within the structure. An image of the structure interior is then derived from the reconstruction of the aforesaid spatial relationships.

Thus, no attempt is made (by guard electrodes or by other means) to restrict the current to flow in a beam-like fashion. As a consequence, the current paths spread and the currents flow throughout substantially the entire region of interest. This general and unrestricted flow of current creates a voltage distribution pattern over the surface of or within the region of interest, that may be measured at all sites over or within such region and not just at those active sites through which current is impressed or withdrawn. This surface voltage distribution is some function of the impedance (i.e. compositional) distribution of the structure. Because of the large numbers of voltage measurement sites available, and because these measurements furnish information relative to the interior of the structure, one may dispense with the very few, inaccurate, voltage measurements that could be obtained at the current input and output sites. The voltage measurements are preferably obtained with high-impedance measuring equipment. Therefore, negligibly small currents are drawn at such sites and, as a consequence, the problem of contact impedance voltage drop is largely avoided.

The inverse problem associated with a single excitation configuration, may not have a unique solution. That is to say, there may be many internal structures that will produce the measured and observed voltage distribution. To reduce the indeterminacy it is necessary to impress a sequence of current-excitation patterns, one pattern at a time or in parallel—for example, by frequency multiplexing. The voltage field distribution is mapped for each case. If sufficient cases are tested, the uncertainty resolves itself to the state where the resultant "pictures" are left with a fuzzy outline, much like the imperfect focus of a camera. Increasing the number of measurements will improve the "focus". For example, if one is taking a tomograph of the thorax, about thirty electrodes could encircle the chest at each of five levels. These 150 electrodes permit 149 linearly independent excitations to be impressed and therefore $149 \times 148 = 22{,}052$ voltage measurements to be made and they could be obtained within a fraction of a second in order to produce a "snapshot" of an impedance distribution in order to image rapidly moving organs and in order to minimize the inconvenience and discomfort experienced by subjects—possibly ill subjects—who would be required to remain motionless while measurements for body images are obtained by prior art techniques. The measurements are made automatically—for example, using signal-averaging procedures. The data is then stored for subsequent computer analysis.

Given a set of comparison signals derived as described above, a computer may be used to "develop" the picture. It does this by finding an internal resistivity distribution within the three-dimensional body that best satisfies—in an average sense—the plurality of measured voltage distribution patterns that result from the sequence of current-excitation patterns. This is done in an iterative fashion. To do the analysis efficiently, a numerical method—such as the finite-difference or finite-element method—is used, coupled with techniques for the efficient solution of the resulting very large systems of equations.

BRIEF DESCRIPTION OF THE DRAWINGS

FIG. 1 is a perspective view of part of a human torso having an electrode array secured thereto for imaging the internal organs of the torso in accordance with a preferred embodiment of the invention;

FIG. 3 shows a cube which is assumed to be excised from a host medium being imaged;

FIG. 5 is a wave-form chart illustrating the operation of the circuit diagrammatically shown in FIG. 4.

DESCRIPTION OF THE PREFERRED EMBODIMENTS

Figure 2:
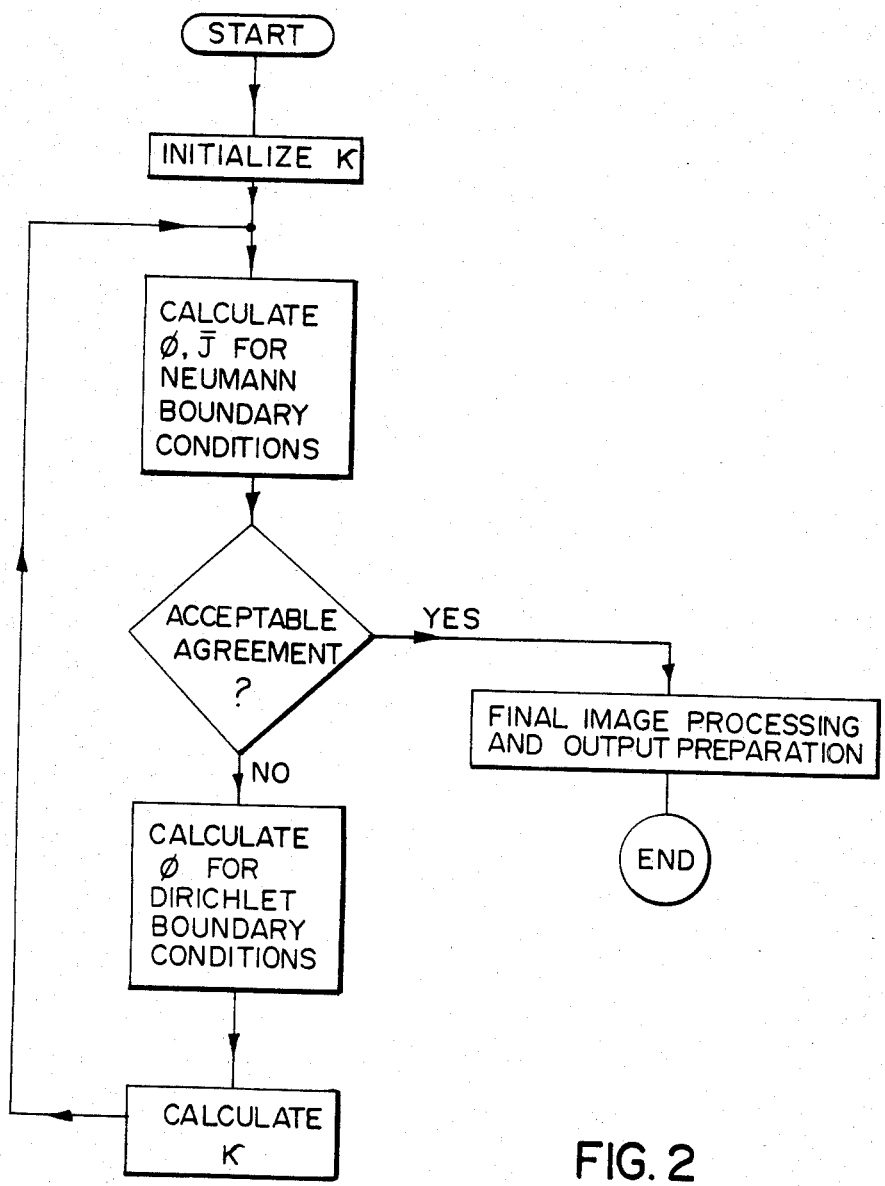
FIG. 2 is a flow chart of an iterative reconstruction algorithm for inputting and measuring signals applied and measured at the electrodes shown in FIG. 1 and for processing the data obtained upon the basis of such measurements to provide an image of the internal body organs.

Referring now to the drawings, and particularly to FIG. 1, a plurality of electrodes 10 are arranged in five horizontally spaced rows, each containing thirty electrodes, in a belt or girdle 11 which may be strapped about the patient's chest 12. A male connector 13 is located on the belt, such connector having a plurality of pins, each of which is individually connected to a respective electrode. The complementary socket 14 of the connector is connected through a multiple-conductor cable 15 to a measurement control and data acquisition apparatus 16 which will hereinafter be described in more detail in connection with FIG. 4. The apparatus 16 is under the control of a computer, which processes the stored data to provide a real-time display or printout of the body being imaged.

The basic differential equation employed in the imaging algorithm is the Poisson equation for continuously inhomogeneous media, i.e.

$$-\nabla \cdot \kappa \nabla \phi = f$$

where $\kappa$, $\phi$ and f are the conductivity, electrical potential and impressed current source distributions respectively within the region being studied. The units are (ohm-m)$^{-1}$, volts and Amperes/m$^3$ respectively. Although, strictly speaking, this equation holds only for the d.c. case, it is applicable to the a.c. case if the conductivity is sufficiently high so that the importance of dielectric effects is negligible. If this condition is not met, then for lower frequencies $\kappa$ must be treated as a complex quantity. For yet higher frequencies, it is expected that a Helmholtz equation would be required—for example $$\nabla \times \nabla \times \bar{E} - \omega^2 \mu \epsilon (1 - j\kappa/\omega\epsilon)\bar{E} = -j\omega\mu \bar{J}_s$$

holds for the case in which the magnetic permeability is not a function of position. $\omega$ is the radian frequency, $\mu$ is the permeability, $\epsilon$ is the permittivity, $\bar{J}_s$ is the impressed current source distribution, $j = \sqrt{-1}$ and $\bar{E}$ is the electric field strength which is a vector quantity. For nonsinusoidal and for rapid variations, a wave equation is required. In this case, one form of such equation is $$\nabla \times \nabla \times \bar{E} + \mu\epsilon \frac{\partial^2 \bar{E}}{\partial t^2} + \mu\kappa \frac{\partial \bar{E}}{\partial t} = -\mu \frac{\partial \bar{J}_s}{\partial t}$$

where, again, the magnetic permeability is constant throughout. When the conduction current is considerably greater than the displacement current then the preceding two equations reduce to $$\nabla \times \nabla \times \bar{E} + j\omega\mu\kappa\bar{E} = -j\omega\mu \bar{J}_s$$

and $$\nabla \times \nabla \times \bar{E} + \mu\kappa \frac{\partial \bar{E}}{\partial t} = -\mu \frac{\partial \bar{J}_s}{\partial t}$$

respectively. In the situations that require the preceding four equations, one must measure the vector $\bar{E}$ rather than the scalar $\phi$. By considering the dual fields, $\bar{H}$ may be measured. Also, one can arrange to measure power density. For purposes of illustrating the computational algorithm (e.g. for subsurface imaging), a three dimensional grid of nodes is defined over a cube (see FIG. 3) considered to be excised from the host medium and includes the region of interest. Each side of the cube is of length 1 and is subdivided into a mesh defined by n points per edge. Thus there are $n - 1$ links or mesh intervals to an edge, each of length $$h = 1/(n-1)$$

Measurement locations are indicated at the top surface. A particular excitation pair is indicated centered at points a and b and a reference node at r. The total current impressed at the electrodes is I.

At the node points, located at mesh intersections, the potentials are computed and the conductivity is then estimated within the intervening regions in a sequential process by which convergence to the conductivity distribution results.

Discontinuous conductivity regions (e.g. bone-tissue interfaces, buried objects, etc.) are blurred and made continuous by limitations of number and accuracy of experimental measurements and practical limitations upon the number of nodes that can be included in the computer model. In this way, the blurring is of the order of the mesh-spacing interval h. Improved discrimination results with improvement of measurement accuracy, with increase of number of excitations and measurements, and with refinement of the mesh.

To produce the image, an iterative approach, involving successive estimates of potential-conductivity-potential etc., is employed as illustrated in the flow-chart of FIG. 2. The sequence of events is as follows:

Step (1)

Calculation of potential $\phi$ and current density $\bar{J}$

Assuming initially a homogeneous medium (or whatever approximation to the conductivity appears reasonable) and subsequently whatever inhomogeneous conductivity distribution results from any subsequent iterative stage, potential $\phi$ and current flux density distribution $\bar{J}$ (Amperes/m$^2$) are computed by solving the previously-described Poisson equation (e.g. by finite-difference or finite-element means).

The interior current distribution, for each excitation case, is calculated by first solving for the interior potentials with the known impressed currents within the region or applied at appropriate surface node locations. In the latter case, the inhomogeneous Neumann boundary condition $$\kappa(s) \frac{\partial \phi}{\partial n} \Big|_s = h(s)$$

is specified. h(s) (Amperes/m$^2$) describes the electrical current flux density entering or leaving the medium over an electrode surface. (The integral of this current flux yields the total current magnitude I.). Where no current is impressed, h(s)=0.

Thus, with $\phi$ obtained, the electrical current flux density distribution is given by $$\bar{J} = -\kappa \nabla \phi$$

which is the application of Ohm's Law. As $\kappa$ is an estimate, $\bar{J}$ is an estimate. However, this computation yields reasonable current flow-line patterns even for very approximate conductivity distributions.

The interior potential distribution, for each excitation case, is then recalculated by solving the problem modelled with the known measured electrode voltages applied at appropriate node locations. The Dirichlet boundary condition is $$\phi(s) = g(s)$$

which corresponds to the measured potentials over the top surface at z=0. A reference potential, located at the point r, is indicated in FIG. 3. (At that point, g(s)=0). This computation yields reasonable potential distribution patterns, even for very approximate conductivity distributions, due to the influence of the applied voltages upon the interior region.

Thus the preceding paragraphs describe the computation of current-flow and potential fields resulting from the imposition of Neumann and Dirichlet boundary conditions respectively. The next step of the algorithm estimates the conductivity distribution $\kappa$ such that approximate compatibility of the Neumann and Dirichlet boundary conditions is attained and explains why this compatibility is required and what is meant by "compatibility" in this context.

Step (2)

Calculation of conductivity

The imposition of the previously-described Ohm's Law, over the interior region, employing both the previously-estimated $\phi$ and $\bar{J}$ (Step (1)), yields a $\kappa$ that permits approximate compatibility of the Neumann and Dirichlet boundary conditions.

Clearly, for a single excitation, a number of widely differing conductivity profiles can be made to satisfy the surface voltage and current boundary conditions. However, the indeterminacy is reduced by employing the multiplicity of excitations and their resulting measurements in this step. Thus, by using an increasing number of linearly-independent excitations, the region of uncertainty is largely contained within a reducing and somewhat fuzzy boundary.

To this end, a least-square technique produces an improved estimate of the conductivity profile—one that satisfies both boundary conditions, for all excitations, in an average sense. Thus, a displacement of the conductivity estimate is caused.

It is known that (for a specified $\kappa$) the Poisson equation yields a unique solution $\phi$ when one boundary condition (whether Neumann or Dirichlet) is specified at each boundary point. From this solution $\phi$, the Neumann and Dirichlet boundary conditions $$\left( \frac{\partial \phi}{\partial n} \Big|_s \right.$$

and $\phi(s)$) can be derived at each boundary point. There is therefore a unique relationship between the pair of boundary conditions and thus the boundary conditions are compatible for a given $\kappa$. However, with boundary conditions corresponding to actual measurements and with $\kappa$ only an estimate of what existed during the measurements, the pair of boundary conditions cannot be expected to produce identical computed internal fields.

Therefore, with J (as calculated from $\phi$ using the impressed currents, i.e. the Neumann boundary condition) and $\phi$ (as calculated using applied voltages, i.e. the Dirichlet boundary condition), Ohm's Law is generally not satisfied. Thus $\bar{J} + \kappa \nabla \phi$ generally does not vanish at all points within the region and thus produces a residual where this term is evaluated. In order to enforce compatibility, the minimization of the square of the residual over all points and for all excitations is sought. It is therefore sought to minimize $$R = \sum_X \int_v (\bar{J} + \kappa \nabla \phi) \cdot (\bar{J} + \kappa \nabla \phi) dv$$

where R is the squared residual sum, V is the region over which the imaging is being performed, and X represents the excitations over which the sum is taken. With conductivity described in terms of $\kappa_i$ over small subregions corresponding to mesh cells, it is therefore required to deduce the conductivity distribution for which $$\frac{\partial r}{\partial \kappa_j} = 0$$

for each i. Solution of the resulting system of equations for all $\kappa_i$, i.e. for the improved estimate of $\kappa$, can be obtained by iterative methods.

Step (3)

Recursive improvement

Using the new estimate, computed in Step (2), the Neumann boundary condition problem is solved for all excitations. The computed boundary potentials are compared with those measured. If the differences are greater than some pre-set tolerance, or if by experience insufficient iterations are known to have been performed, then the process continues with the Dirichlet boundary condition problem of Step (1). Otherwise the process continues to Step (4).

Step (4)

Final image processing and presentation

Procedures including histogram adjustment, edge detection, and other image enhancement techniques, and surface modelling for three-dimensional presentation, are employed at this stage. Finally, results are presented on a video or a paper-copy terminal. Processed data may be stored on magnetic disk for future reference.

As an alternative to the foregoing sequence of steps, it is possible to operate directly upon the measured and calculated surface voltages in order to reduce the difference between their values by adjustment of the interior conductivity distribution. Optimization methods, such as gradient methods, can be used to this end.

Figure 4:
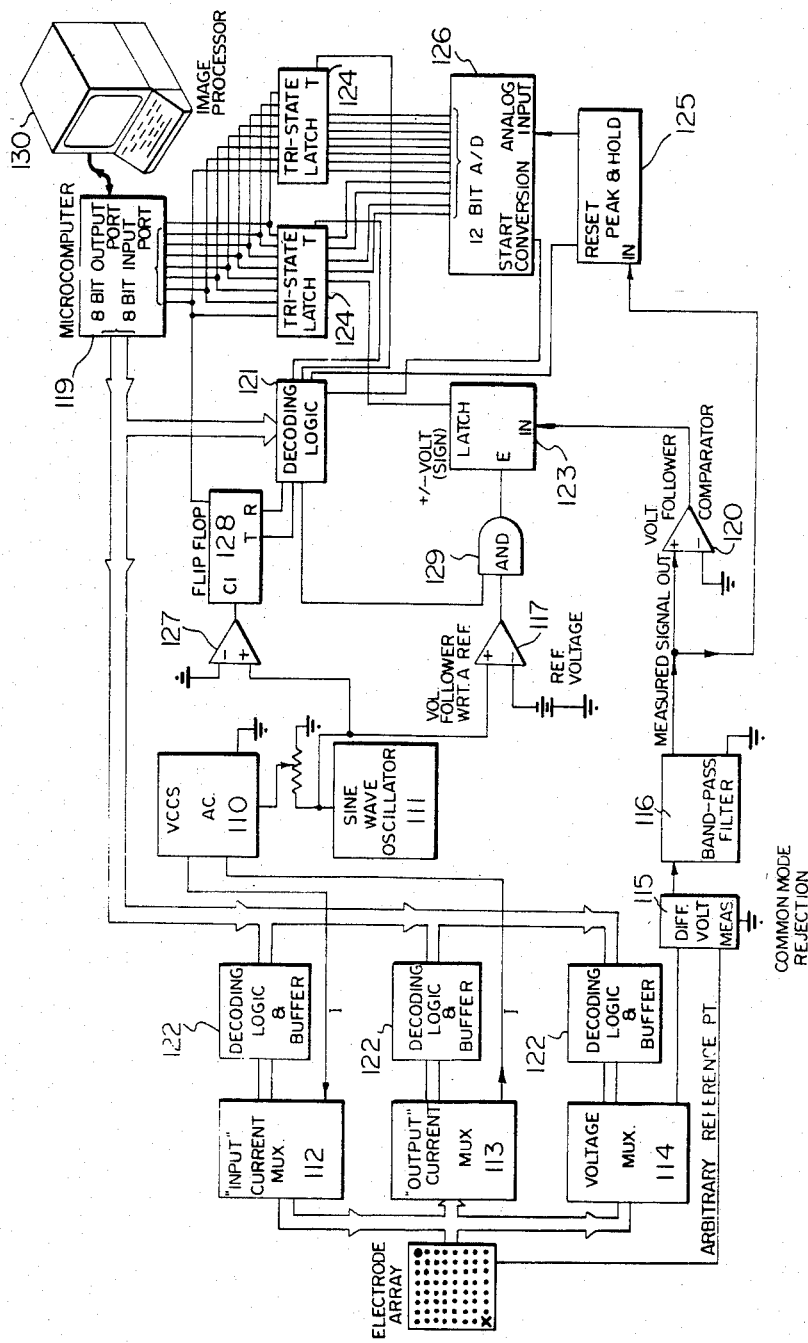
FIG. 4 is a block diagram of a measurement control and data acquisition system for implementation of the imaging method of the invention.

Referring now to FIG. 4, there is shown a block diagram of one hardware configuration employed in the data acquisition system. A voltage-controlled current source 110 receives an input from a sine-wave oscillator 111. The current leads are attached to input current and output current multiplexers 112 and 113, respectively. A lead for measured voltage is connected to a voltage multiplexer 114. The selection of input, output or voltage site for excitation and for measurement purposes is controlled, in the first place, by two bits of an eight-bit word sent from a microcomputer 119 8-bit output port. Thus, any one of three decoding and logic buffers 122 is addressed and the associated decoding logic causes the buffer to be enabled and the remaining bits to be latched in that particular buffer. These 6 bits specify one of the 64 electrodes of the girdle or electrode array 11 (see FIG. 1) to which the excitation current is directed or at which the voltage measurement is taken. (Extension of this system to more or to fewer electrodes will be readily apparent to those skilled in the art). In sequence, the computer 119 causes the input and output node addresses to be latched and thus directs the current, via multiplexers 112 and 113 and the appropriate electrodes, through the body being imaged. Two 8-bit words are required for this operation. Similarly, the voltage multiplexer 114 is addressed and a selection of a voltage measurement site is made using another 8-bit word. Finally, the remaining device that can be addressed, using the two bits previously mentioned, is a tri-state decoding logic device 121.

The voltage-controlled current source 110 receives an input signal from the sine-wave oscillator 111. Current input and output sites and the voltage measurement site are selected as previously described. The voltage at the selected measurement site is measured by means of a differential amplifier 115, the output of which is channeled through a band-pass filter 116. A voltage follower 117 is arranged such that it is turned on only when the positive peak of the oscillator is greater than the reference voltage. Likewise, a voltage follower comparator 120 is turned on only when its input signal is positive. If the tri-state decoding logic device 121 sends a positive signal to an AND gate 129 and voltage follower 117 does likewise, then the sign latch 123 is enabled, thus latching the output of comparator 120. Thus, if the signal measured is in phase with the oscillator, a "1" is latched. If it is not in phase, a "0" is latched. This sign bit is then directed to the most significant byte of tri-state data latches 124.

The voltage from band-pass filter 116 is directed to a peak-and-hold detector 125, thence to a 12-bit analog-to-digital converter 126. Upon a signal being received from the decoding logic device 121, digital conversion of the analog signal is performed with the output directed to the tri-state data latches 124. These two bytes of data are read by the microcomputer in time sequence.

An amplifier 127 changes the sine wave output from oscillator 111 to a square wave. The positive-going edge triggers a flip-flop 128 setting the output high and so, when detected by the computer 119, initiating a sequence of events (see FIG. 5) beginning just after time "a". The sequence of events illustrated in FIG. 5 occurs under control of computer 119.

The output from microcomputer 119 is applied to an image processor 130, for implementing the algorithm hereinbefore described. The image processor is configured to drive a video display or other display. Thus, it may be seen that the microcomputer has essentially a dual purpose—to control the selection of current injection and withdrawal sites and voltage measurement sites and to feed the measured digitized data to an image processor. Alternatively, the microcomputer could be eliminated and its functions performed by the computer part of the image processor.

In the example given, the voltage measurement and current injection and withdrawal electrodes are located externally of the body being imaged. For obvious reasons, such an arrangement is usually desirable for imaging human or animal bodies. However, particularly for geological work or other situations where the body being imaged is inanimate, it may be desirable to employ buried electrodes. In any event, the basic measurement and computational techniques employed are essentially the same.

Also, the example given employs time sequence multiplexers for selection of current injection and voltage measurement sites. In fact, the current injection may be performed by means of frequency multiplexing whereby measurements may be taken in parallel.

Typical Components which may be used in the system of FIG. 4 are as follows:

FIG. 4

| Ref. No. | Description of the Parts | Manufacturer | Part Number |
| --- | --- | --- | --- |
| 112; 113; 114 | Multiplexers (eight each) | PMI | MUX-08-EQ |
| 122; 124; 128 | Octal D-type transparent latches | TI | 74LS373N |
| 121; 122 | Decoders | TI | 74LS138N |
| 121 | | TI | 74LS139 |
| 122 | Dual monostable multivibrators | TI | 74LS221N |
| 110; 115 | Operational amplifiers | Natl. | LM356 |
| 117; 120; 127 | | Natl. | LM111 |
| 125 | | PMI | OP-06 |
| 116 | Band-pass filter | Natl. | AF150 |
| 111 | Oscillator | EXAR | 2206 |
| 129 | AND gate | TI | 74LS08 |
| 121 | NAND gate | TI | 74LS12 |
| 123 | 4-bit bistable latch | TI | 74LS75N |
| 126 | 12-bit analog-to-digital converter | Natl. | ADC1210 |
| 125 | Sample and hold | PMI | SMP-11FY |
| 125 | Comparator | PMI | CMP-01 |

Manufacturer code:
TI — Texas Instruments
PMI — Precicion Monolithic Incorporated
Natl. — National Semiconductor
EXAR — EXAR Integrated Systems Inc.

For purposes of electrical power supply isolation, for medical applications the following devices from Burr-Brown were used: 722, 3652HG and 2302MC.

In place of the band-pass filter, the reset peak and hold, and associated electronics, the synchronous demodulation technique (e.g. using the GAP01 by PMI) can be used.

As will be appreciated from a consideration of the foregoing, the technique and apparatus of the invention are applicable to the imaging of substantially any sub-surface structure. Indeed, the invention provides a means of at least ameliorating the practical difficulties set forth in the foregoing quotation from the Applied Geophysics textbook in that the "noise level" referred to is not objectionable and actually provides useful rather than confusing information, from which an image may be formed. Also, by virtue of the measurement techniques employed, the invention does not require constant rearrangement of several electrodes and long wires over rough wooded terrain for successful geological and mineral prospecting. Once the wires and electrodes are in place they may be fixed in that location for the entire series of measurements and the large number of measurements performed electronically rather than by manual rearrangement of the wires and electrodes.

It will be understood that the above description of the present invention is susceptible to various modifications, changes and adaptations, and the same are intended to be comprehended within the meaning and range of equivalents of the appended claims.

What is claimed is:

1. A method of displaying an image of the interior of a structure having a plurality of surfaces and comprising regions of different conductivities which differentially affect electrical signals transmitted therethrough, said method comprising the steps of:

(a) applying electrical input currents at a plurality of selected current input sites of said structures, each of said electrical input currents flowing within at least one of said regions and exiting from said structure at a selected current output site thereof;

(b) measuring the voltages generated by each of said applied currents at a plurality of selected voltage measuring sites of said structure with respect to a voltage reference point, each of said selected voltage measuring sites being remote from the current input and output sites through which flows the current generating said voltages;

(c) calculating the voltages $\phi$ at a plurality of locations within said structure, including said selected voltage measuring sites, with respect to said voltage reference point from the equation $$-\nabla\cdot\kappa\nabla\phi=f,$$

where $\kappa$ is a value of conductivity assumed for each of said locations and f is the density of each of the electrical input currents at said current input and output sites, the current traversing the surfaces of said structure except at said current input and output sites being assumed equal to zero;

(d) calculating the electrical current flux density $\bar{J}$ at each of the locations for which the voltage was calculated in step (c) from the equation $$\bar{J}=-\kappa\nabla\phi;$$

(e) comparing the voltages calculated in step (c) for each of said selected voltage measuring sites of said structure and the corresponding voltages measured at said selected sites in step (b);

(f) repeating steps (c) and (d) when the difference between the voltages compared in step (e) are greater than a predetermined amount, the voltages measured in step (b) then being substituted at said selected voltage measuring sites for the voltages calculated in step (c);

(g) calculating new values for $\kappa$ for each of said locations when the squared residual sum R equals $$\sum_X \int\int_V (\bar{J}+\kappa\nabla\phi)\cdot(\bar{J}+\kappa\nabla\phi)\,dv$$

where V is the region over which the imaging is being performed and X represents the excitations over which the sum is taken, by determining the values of $\kappa$ which minimize R throughout said structure;

(h) repeating steps (f) and (g) until the voltages compared in step (e) do not exceed said predetermined amount; and (i) displaying the values of κ calculating in step (h) thereby providing an image of the interior of said structure.

2. The method of claim 1, wherein said electrical input currents are applied in time sequence.

3. The method of claim 1, wherein said electrical input currents are applied in parallel by frequency multiplexing.

4. The method of claim 1, wherein the amplitude of each voltage is measured.

5. The method of claim 4, wherein the phase of each voltage is also measured.

6. Apparatus for displaying an image of the interior of a structure having a plurality of surfaces and comprising regions of different conductivities which differentially affect electrical signals transmitted therethrough, comprising a plurality of unguarded electrodes located at selected sites of said structure, a first group of said electrodes functioning as input electrodes during a given interval of time and a second group of said electrodes functioning as output electrodes during said given interval;

means for applying electrical currents during said given interval to said first group of electrodes, said electrical currents flowing within at least one of said regions;

means for withdrawing said electrical currents from said structure during said given interval at said second group of electrodes;

means for selecting during said given interval a plurality of voltages measuring sites of said structure, said voltage measuring sites being remote from the sites selected during said interval for said first and second groups of electrodes;

means for measuring the voltages at said selected plurality of voltages measuring sites with respect to a voltage reference point, said measurements being made during said given interval;

computer means for (1) calculating the voltages $\phi$ at a plurality of locations within said structure, including said selected voltage measuring sites, with respect to said voltage reference point from the equation $$-\nabla \cdot \kappa \nabla \phi = f,$$

where κ is a value of conductivity assumed for each of said locations and f is the density of each of the electrical input currents at said current input and output sites, the current traversing the surfaces of said structure except at said current input and output sites being assumed equal to zero;

(2) calculating the electrical current flux density $\bar{J}$ at each of the locations for which the voltage was calculated from the equation $$\bar{J} = -\kappa \nabla \phi;$$

(3) comparing the calculated voltages with the voltages measured at said plurality of selected voltage measuring sites; and (4) iteratively calculating new values of the conductivity κ for each of said locations when the squared residual sum R equals $$\sum_X \int \int_V (\bar{J} + \kappa \nabla \phi) \cdot (\bar{J} + \kappa \nabla \phi) \, dv$$

where V is the region over which the imaging is being performed and X represents the excitations over which the sum is taken, by determining the values of κ which minimize R throughout said structure; and display means for displaying the values of conductivity κ thereby producing an image of the interior of said structure.

7. Apparatus as claimed in claim 6, wherein said means for measuring the voltages at said selected plurality of voltage measuring sites measures the amplitudes of said voltages.

8. Apparatus as claimed in claim 7, wherein said means for measuring the voltages at said selected plurality of voltage measuring sites also measures the phase of each of said voltages.

9. Apparatus as claimed in claim 6 wherein said means for applying and withdrawing electrical currents comprises a signal generating source;

a voltage-controlled current source having its input coupled to the output of said signal generating source, and input and output current multiplexers coupling the output of said voltage-controlled current source to said first and second groups of electrodes.

10. Apparatus as claimed in claim 9 wherein said means for selecting said voltage measuring sites and measuring the voltages at said sites comprises at least one voltage multiplexer and a differential amplifier, respectively, said voltage multiplexer coupling electrodes at said voltage measuring sites to the input of said differential amplifier for measurement of the amplitudes of the voltages at said voltage measuring sites with respect to said voltage reference point.

11. Apparatus as claimed in claim 10 which further comprises a band-pass filter coupled to the output of said band-pass filter, and a storage means coupled to the output of said differential amplifier for storing said measured voltage.

12. Apparatus as claimed in claim 11 which further comprises an analog-to-digital converter for receiving the contents of said storage means.

13. Apparatus as claimed in claim 12 which further comprises a comparator, the output of said band-pass filter being connected to said comparator for determining the polarity of the output signal from said filter relative to a reference ground potential.

14. Apparatus as claimed in claim 13 which further comprises tri-state latches, said tri-state latches being connected to the respective outputs of said comparator and said analog-to-digital converter for storage of said determined polarity voltage and the converted voltage from said converter.

15. Apparatus as claimed in claim 14 wherein said computer means reads the contents of said tri-state latches, processes said contents and generates an output therefrom to drive said display device.

16. Apparatus as claimed in claim 15 which further comprises logic decoding and buffer means, said computer means controlling said input and output current multiplexers and said voltage multiplexer through said logic decoding and buffer means for selection of said electrodes for current injection, current withdrawal and voltage measurement.

17. Apparatus as claimed in claim 6 wherein said means for selecting said voltage measuring sites and measuring the voltages at said sites comprises at least one voltage multiplexer and a differential amplifier, respectively, said voltage multiplexer coupling electrodes at said voltage measuring sites to the input of said differential amplifier for measurement of the amplitudes of the voltages at said voltage measuring sites with respect to said voltage reference point.

18. Apparatus as claimed in claim 17 which further comprises means for measuring the phase of each of said voltages.

* * * * *